(12) United States Patent
Dill et al.

(10) Patent No.: US 7,802,478 B2
(45) Date of Patent: Sep. 28, 2010

(54) METHODS AND APPARATUS FOR MEASURING ELASTIC MODULUS OF NON-SOLID CERAMIC MATERIALS BY RESONANCE

(75) Inventors: Robert J. Dill, Watkins Glen, NY (US); David V. Hayes, Corning, NY (US); John D. Helfinstine, Big Flats, NY (US); Timothy A. Roe, Corning, NY (US); William P. Vann, Beaver Dams, NY (US); David C. Ward, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 464 days.

(21) Appl. No.: 11/823,138

(22) Filed: Jun. 27, 2007

(65) Prior Publication Data

US 2009/0000378 A1    Jan. 1, 2009

(51) Int. Cl.
*G01N 29/12*    (2006.01)
(52) U.S. Cl. .......................................... 73/579; 73/583
(58) Field of Classification Search .................. 73/579, 73/583
See application file for complete search history.

(56) References Cited

U.S. PATENT DOCUMENTS

| | | | | |
|---|---|---|---|---|
| 4,323,614 A * | 4/1982 | Gulati | ......................... | 428/116 |
| 5,168,503 A | 12/1992 | Maeda | ......................... | 372/22 |
| 5,846,891 A | 12/1998 | Son et al. | ...................... | 501/127 |
| 6,372,677 B1 | 4/2002 | Nose et al. | .................. | 501/119 |
| 6,753,277 B2 | 6/2004 | Terashi | ......................... | 501/32 |
| 7,015,161 B2 | 3/2006 | Zou | ............................... | 501/5 |
| 7,047,809 B2 | 5/2006 | Cobb | ........................... | 73/579 |
| RE39,120 E | 6/2006 | Sechi et al. | ..................... | 501/9 |
| 7,067,085 B1 | 6/2006 | Sugawara et al. | ............ | 264/676 |
| 7,072,476 B2 | 7/2006 | White et al. | ................... | 381/74 |
| 7,112,549 B2 | 9/2006 | Yoshitomi et al. | ............ | 501/128 |
| 7,165,463 B2 | 1/2007 | Liu et al. | ....................... | 73/861 |
| 7,179,516 B2 | 2/2007 | Ichikawa | ..................... | 428/116 |
| 7,520,911 B2 * | 4/2009 | Beall et al. | ..................... | 55/523 |
| 2007/0056952 A1 | 3/2007 | Itakura et al. | ............. | 219/444.1 |
| 2007/0082174 A1 | 4/2007 | Masukawa et al. | ........... | 428/116 |

OTHER PUBLICATIONS

ASTM International, "Standard Test for Dynamic Young's Modulus, Shear Modulus, and Poisson's Ratio for Advanced Ceramics by Sonic Resonance", C 1198-1 (Jun. 2001), 251-260.
Boccaccini, D. N., et al., "Determination of thermal shock resistance in refractory materials by ultrasonic pulse velocity measurement", Journal of the European Ceramic Society 27 (2007) 1859-1863.
Latella, Bruno A., et al., "High-Temperature Young's Modulus of Alumina During Sintering", J. Am. Ceram. Soc., 88 [3] 773-776 (2005).

(Continued)

*Primary Examiner*—John E Chapman
(74) *Attorney, Agent, or Firm*—Susan S. Wilks

(57) ABSTRACT

The present invention pertains to apparatus and methods for measuring elastic modulus (Young's modulus) of non-solid materials, including honeycomb ceramic materials used in the filtration and/or treatment of exhaust gasses, through a range of temperatures.

18 Claims, 11 Drawing Sheets

OTHER PUBLICATIONS

Dickson, R.W., et al., "An Alumina Standard Reference Material for Resonance Frequency and Dynamic Elastic Moduli Measurement I. For Use at 25° C.", Journal of Research of the National Bureau of Standards—A. Physics and Chemistry, vol. 75A, No. 3, May-Jun. 1971, 155-162.

Ikeda, S., "A Measure to Estimate the Effectiveness of Weight Series and Weighing Designs for the Minimization of Propagated Adsorption Errors", Metrologia 22, 69-74 (1986).

Baveja, K.D., "Dynamic method of measuring Young's modulus of elasticity", J. Sci. Instrum., 1964, vol. 41, 662-665.

Sorrentino, Francois, "Equipment for Measurement of Elasticity Modulus for Hot Cell Applications", The Review of Scientific Instruments, vol. 42, No. 2, 191-192, (Feb. 1971).

ASTM International, "Standard Test Method for Young's Modulus, Shear Modulus, and Poisson's Ratio for Glass and Glass-Ceramics by Resonance", C 623-92 (2005) 1-7.

ASTM International, "Standard Test Method for Moduli of Elasticity and Fundamental Frequencies of Carbon and Graphite Materials by Sonic Resonance", C 747-93 (2005) 1-8.

ASTM International, "Standard Method for Young's Modulus, Shear Modulus, and Poisson's Ratio for Ceramic Whitewares by Resonance", C 848-88 (2006), 1-7.

ASTM International, "Standard Test Method for Young's Modulus of Refractory Shapes by Sonic Resonance", C 885-87 (2007) 1-6.

ASTM International, "Standard Test Method for Dynamic Young's Modulus, Shear Modulus, and Poisson's Ratio for Advanced Ceramics by Sonic Resonance", C 1198-01, 1-11, (2001).

ASTM International, "Standard Test Method for Dynamic Young's Modulus, Shear Modulus, and Poisson's Ratio of Refractory Materials by Impulse Excitation of Vibration", C 1548-02 (2007), 1-7.

ASTM International, "Standard Test Method for Dynamic Young's Modulus, Shear Modulus, and Poisson's Ratio by Sonic Resonance", E 1875-00, 1-8, (2001).

ASTM International, "Standard Test Method for Dynamic Young's Modulus, Shear Modulus, and Poisson's Ratio by Impulse Excitation of Vibration", E 1876-07, 1-15, (2007).

JIS R 1602-1986 "Testing Methods for Elastic Modulus of High Performance Ceramics", 1-11, (1986).

ASTM International, Spinner, S., et al., "A Method for Determining Mechanical Resonance Frequencies and for Calculating Elastic Moduli from these Frequencies", vol. 61, 1961, 1221-1238.

Lostak, F., et al., "Determination of the Elastic Moduli of Materials at High Temperatures by Means of a non-contact Sensor", 1-6.

Weiler, Bernd, et al., "Elastic Constants—Their Dynamic Measurement and Calculation", 1-16.

Zhang, J., et al., "New technique for measuring the dynamic Young's modulus between 295 and 6 K", Cryogenics 1991, vol. 31 October, 884-889.

ASTM International, "Standard Test Method for Fundamental Transverse, Longitudinal, and Torsional Resonant Frequencies of Concrete Specimens", C 215-02, 1-7, (2003).

* cited by examiner

PRIOR ART

METHODS AND APPARATUS FOR MEASURING ELASTIC MODULUS OF NON-SOLID CERAMIC MATERIALS BY RESONANCE

BACKGROUND OF THE INVENTION

The present invention pertains to methods for measuring physical characteristics of materials. More particularly, the present invention relates to methods for measuring elastic modulus (Young's modulus) of ceramic materials, including complex non-solid ceramics or glass-ceramics, through a range of temperatures.

Porous ceramic honeycomb structures are widely used as catalytic converter substrates and diesel particulate filters (DPFs). These structures may be formed from porous ceramic material, such as silicon carbide, cordierite or aluminum titanate. The earliest cordierite ceramic honeycombs for these applications consisted of reaction-sintered cordierite substrates prepared from extruded mixtures of talc, kaolin, calcined kaolin, and alumina. These were found to have suitable chemical durability, inertness, refractoriness, thermal shock resistance, and other properties for the application, and were cost effective to manufacture. Cordierite is a ceramic composition of the formula $Mg_2Al_4Si_5O_{18}$. Cordierite can exist in many crystalline forms including orthorhombic cordierite (orthorhombic $Mg_2Al_4Si_5O_{18}$ and its solid solutions), indialite (hexagonal $Mg_2Al_4Si_5O_{18}$ and its solid solutions), and mixtures thereof.

Recent trends in exhaust after-treatment for both gasoline and diesel engines have placed greater demands on converter and DPF materials. For converters, the shift toward higher cell densities and thinner walls has created material challenges in meeting requirements for strength and erosion resistance. The most recent applications requiring low cell densities and thin walls for reduced back pressure offer similar challenges, as does the growing interest in higher porosity converters with lower thermal mass for faster light-off to meet emission standards. Lower back pressure creates higher efficiency filters, while faster light-off reduces emissions when an engine is started and the filter is cold.

Demand for materials that can withstand these increasingly challenging conditions requires an increasingly detailed understanding of the chemical and physical characteristics of these materials under a wide range of conditions. In addition, it is desirable to understand the physical characteristics of materials during a manufacturing process, so that deviations from standard or desired characteristics can be identified early in a manufacturing process, to eliminate waste and improve quality control in manufacturing.

SUMMARY OF THE INVENTION

In embodiments, the present invention provides a method for measuring the elastic modulus, or Young's modulus, of a non-solid ceramic material includes the steps of: 1) generating a frequency-controlled electrical signal from an amplifier; 2) using a signal transducer such as a minishaker to transform the electrical signal into a mechanical signal; 3) introducing the mechanical signal to a suspended non-solid ceramic specimen via a length of silica yarn causing the specimen to resonate at a resonance frequency; 4) communicating the resonance frequency to a pickup transducer via a second length of silica yarn, allowing the pickup transducer to transform the resonance vibration signal into an electrical signal; 5) measuring the peak resonance frequency; and, 6) calculating the elastic modulus based on the dimensions of the specimen, the measured peak resonance frequency, and the Poisson's ratio of the material.

In additional embodiments, the present invention provides a method of measuring the elastic modulus of a non-solid ceramic material including the steps of suspending a non-solid ceramic material from two silica threads; delivering a vibration signal to the non-solid ceramic material through one silica thread across a range of frequencies; and measuring a vibration signal from the non-solid ceramic material through another silica thread across a range of frequencies. Further embodiments may provide taking the measurements through a range of temperatures between 20° C. and 1200° C., and from 1200° C. and 20° C.

In further embodiments, the vibration signal may be provided by a minishaker and may be delivered to a pickup transducer which is a modified earphone. In embodiments the silica yarn is between 0.005 and 0.5 inches in diameter. In still further embodiments, the silica yarn is 0.02 inch diameter SY1-UC silica yarn available from EMTECH or Saint-Gobain Quartzel® thread 300-2/4 QS13 4Z 3.8S.

In additional embodiments, the invention provides a method for measuring the elastic modulus of a non-solid ceramic material including the steps of suspending a non-solid ceramic material by at least two silica threads in an oven; heating the ceramic material through a range of temperatures range between 20° C. and 1200° C.; delivering a vibration signal to the non-solid ceramic material through one silica thread through a range of frequencies; and, measuring a vibration signal from the non-solid ceramic material through another silica thread across the ranges of frequencies and temperatures; and displaying the measured vibration signal across the ranges of frequencies and temperature.

In still further embodiments, the present invention provides an apparatus for the measurement of elastic modulus in a non-solid ceramic material having a minishaker vibration generator; a first and a second length of silica yarn of between 0.005 and 0.5 inches in diameter and between 8 and 15 inches in length, each having a loop at each end; a modified earphone pickup transducer; where one end of one length of silica yarn is connected to the minishaker vibration generator and one end of the other length of silica yarn is connected to the modified earphone pickup transducer; where a sample of non-solid ceramic material is suspended in the loops of the two lengths of silica yarn; whereby when a vibration signal is generated by the minishaker, the signal is transmitted to the non-solid ceramic material through the one length of silica yarn causing the non-solid ceramic material to resonate, and whereby the resonance frequency is communicated to the modified earphone pickup transducer via the other length of silica yarn.

BRIEF DESCRIPTION OF THE DRAWINGS

The invention is further described below with reference to the appended drawings, wherein.

DETAILED DESCRIPTION

Figure 1:
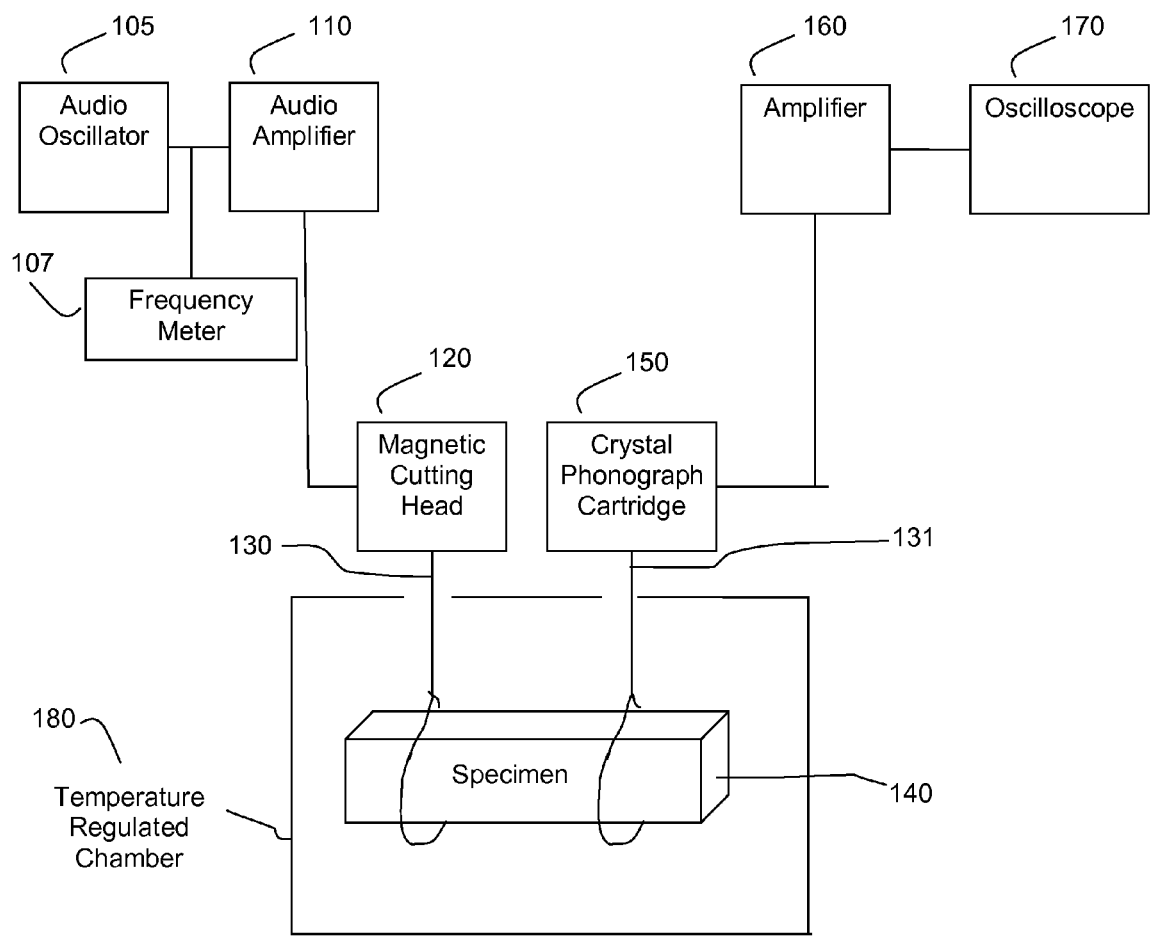
FIG. 1 is block diagram of a comparative test apparatus for measuring the elastic modulus of a solid ceramic material.

The present invention encompasses methods and apparatus for measuring the elastic modulus (Young's modulus) of non-solid ceramic materials through a range of temperatures. More specifically, the present invention provides improved methods and apparatus for measuring the elastic modulus of non-solid ceramic honeycomb substrates used in the production of diesel exhaust filters, such as catalytic converters, at high temperatures. Apparatus and methods of the present invention are usable at high temperatures during or in parallel with high temperature steps of a manufacturing process for ceramic honeycomb substrates. These measurements can be taken early in the manufacturing process for ceramic honeycomb substrates.

While there are standard techniques available to measure physical characteristics of materials such as thermal-shock, modulus of rupture (MOR), Young's modulus or elastic modulus (E) and coefficient of thermal expansion (CTE), there is a need for techniques to measure these characteristics of materials, including complex non-solid ceramic materials more accurately and reliably, using equipment that provides improved functionality in a wider range of conditions. In addition, there is a need to measure physical characteristics of increasingly complex materials having irregular, non-solid and/or anisotropic characteristics. Techniques that can be used throughout a manufacturing process, including through high temperature conditions, are also desirable.

Measuring the elastic moduli of materials is critical for predicting the behavior and reliability of objects made from that material. However, known techniques for these measurements are designed for solid homogeneous materials. These known techniques range from tensile stretching, to timing sound pulses through the material, to vibrating the material like a tuning fork. Various standards (ASTM C1198-01, ASMT C623-92 (2005), JIS R 1602 (1986), etc.) as well as technical papers and books and training courses can be found to describe these methods. Measurements of the elastic moduli of ceramic honeycomb substrates and filters, where the ceramic materials are porous and anisotropic, and where the structures are non-solid, honeycomb-shaped or irregularly shaped, are significantly more complicated than standard measurements. These materials do not transmit sound waves or vibration signals as readily as solid isotropic materials. The resonance of these materials may be more challenging to measure. They require more sensitive methods and apparatus than the standard known methods.

High temperature measurements of elastic modulus in ceramic honeycomb materials create additional experimental challenges. The apparatus used in high temperature applications must be sensitive enough to enable measurements of subtle vibration signals in complicated systems, and must also withstand a hostile high temperature environment. High temperature measurements of these complex materials are valuable in that they allow for monitoring of the physical characteristics of ceramic materials as they go through the conditions that the materials might experience during manufacturing processes or in use, including exposure to high temperatures. The ability to test and monitor the status of manufactured materials during all phases of the manufacturing process allows for more careful quality control, and reduces waste in the manufacturing process. For example, if an elastic modulus measurement taken in conditions that mimic a manufacturing process indicate that the material loses its integrity or cracks under those conditions, the source of those imperfections can potentially be pinpointed in the manufacturing process. For example, if cracks or flaws occur in a ceramic honeycomb structure during a heating step or a cooling step, these defects can be identified by taking the material through those steps experimentally. Or, test specimens can be monitored during actual manufacturing steps. More precise measurement procedures allow for more precise and efficient quality control measures during a manufacturing process.

In addition, where materials are exposed to extremes of temperature during normal use, as is the case for ceramic honeycomb filters, the ability to characterize these materials through a range of temperature extremes is helpful in determining the characteristics of the materials throughout their intended use. For example, it is useful to know if the elastic modulus of a ceramic material changes significantly through a range of temperatures, especially if the material will experience that range of temperatures during normal use. An understanding of those physical material changes is useful in developing products with desired material characteristics.

Elastic modulus, or Young's modulus, is one measure of the physical characteristic of material related to its ability to deform, instantaneously and uniformly, in response to and proportionally to the application of a force or stress. When the stress is removed, the material will return to its original size and shape without a loss of energy. Elastic modulus is a measure of a material's rigidity. Elastic modulus is generally given the symbol "E." There are many methods for measuring the elastic modulus, or "E" of a material including tensile stretching, timing sound pulses through the material or vibrating the material like a tuning fork.

In a simple example, one way to measure the elastic modulus is to apply a stress ($\sigma$) to a material, where the stress ($\sigma$) is defined as the force (F) applied over the cross-sectional area (A) of a material:

$$\sigma = F/A. \quad \text{Formula 1}$$

The strain ($\epsilon$) of a material can be assessed by measuring the change in the length of a material after the application of the stress ($\sigma$).

$$\epsilon = (l_1 - l_0)/l_0, \quad \text{Formula 2}$$

Figure 12:
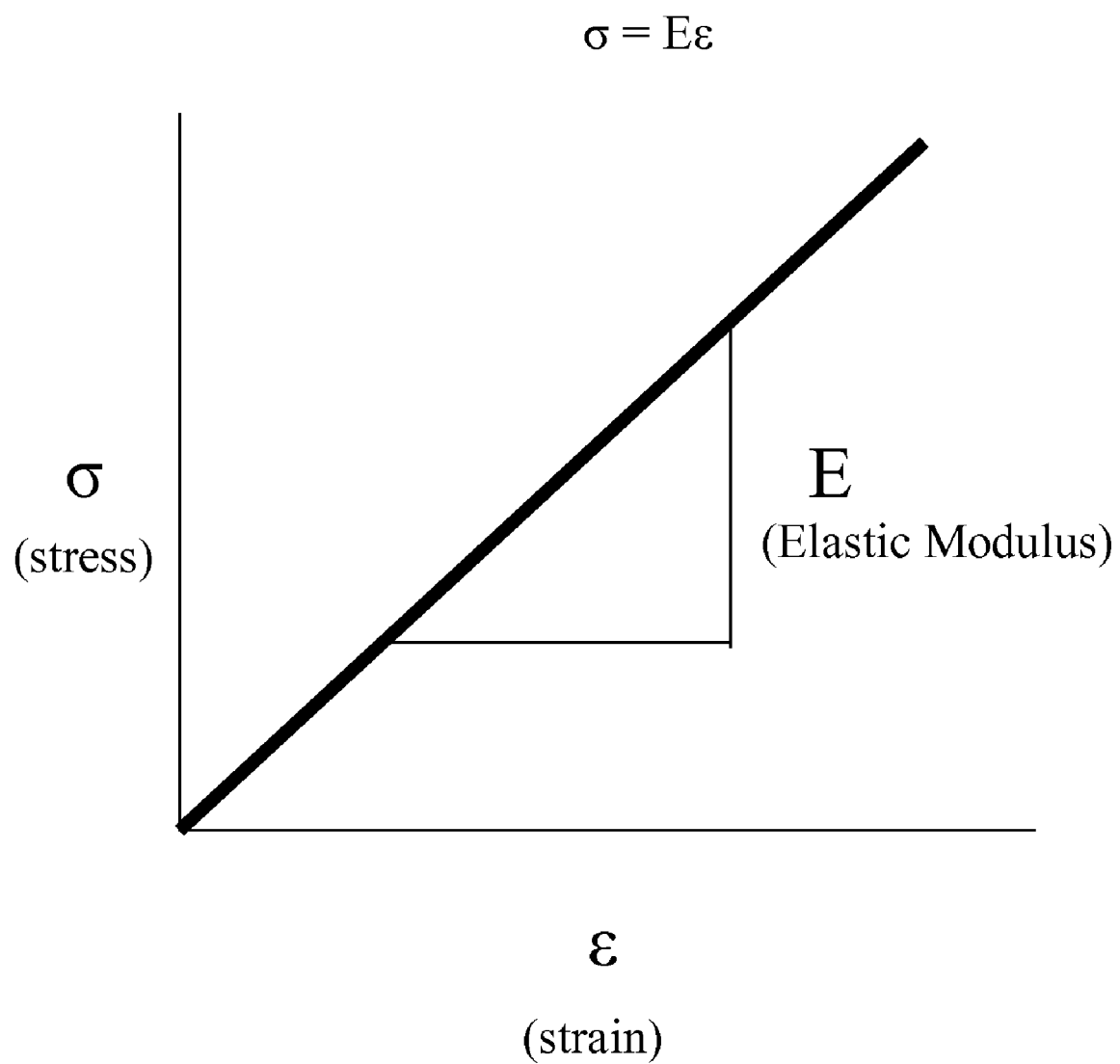
FIG. 12 is a graph showing a plot of stress ($\sigma$) versus strain ($\epsilon$), where the slope (E) is the elastic modulus.

In a plot of stress versus strain, the slope of the line is the elastic modulus (see FIG. 12).

$$\sigma = E\epsilon. \quad \text{Formula 3}$$

For many materials, this type of measurement is impractical to implement experimentally. For example, it is not always practical to measure a change in length of a material. And, some materials are too brittle to lend themselves to this type of measurement. Alternative methods for measuring the elastic modulus have been described in standard testing methods promulgated by organizations such as the American Society for Testing and Materials (ASTM), the Japanese Industrial Standard (JIS), and the German standards organization, Deutsches Institut fur Normung (DIN).

ASTM standards C623-92 (2005) and C1198-01 (2001), among others, describe methods for testing Young's Modulus by resonance. ASTM Standard C623-92 (2005) describes a standard test method for Young's modulus for glass and glass-ceramics by measuring resonance. The method described in C623-92 is suitable for solid isotropic (having elastic properties that are the same in all directions in the material) specimens.

These methods introduce a vibration signal to a specimen. This vibration signal, at a specific frequency, causes the specimen to resonate. This innate resonance will be specific for that frequency of introduced signal at that temperature, and specific for that specimen having its own unique geometric and material properties, including the degree to which that specimen can deform in response to a stimulus, or its elastic or Young's modulus.

The methods described in ASTM C623-92 (2005) and ASTM C1198-01 measure resonance frequencies of solid specimens of material having a specific geometry. FIG. 1 illustrates a measurement apparatus described in ASTM C623-92 (2005) and ASTM 1198-01 as a comparative example to the method and apparatus of the present invention. In FIG. 1, an audio amplifier 110 provides an electrical signal to a magnetic cutting head 120 which converts the electrical signal from the audio amplifier to a mechanical, vibration signal. The audio amplifier may have a continuously variable frequency output between 100 Hz to 20 kHz. The magnetic cutting head 120 is coupled to a string 130 which suspends the specimen 140. Another string 131 used to suspend the specimen 140 is coupled to a crystal phonograph cartridge 150 which translates the mechanical vibration signal into a digital signal. The digital signal is then amplified by an amplifier 160 and displayed on an oscilloscope 170. The amplifier should be impedance matched with the crystal phonograph cartridge (the detector transducer) and an audio oscillator 105 having a continuously variable frequency output from between 100 Hz and 20 kHz and low drift may be used to generate a sinusoidal voltage to the audio amplifier 110. In addition, a frequency meter 107 may be provided to monitor the audio oscillator 105 output to ensure that that the frequencies provided to the magnetic cutting head 120 via the audio amplifier 110 are accurate. The specimen 140 may be suspended in a temperature regulated chamber 180 such as a cryogenic chamber or a furnace.

An electrical signal, originating through the audio amplifier 110 is transmitted to the magnetic cutting head 120 or the driver transducer, through the first string 130 to the specimen 140. The specimen 140 resonates in response to the applied mechanical frequency as a function of the vibration signal applied to it and the specimen's elastic modulus (E). The specimen 140 resonance vibration is transmitted to the crystal phonograph cartridge 150 via the second length of string 131 where the mechanical vibration signal is translated back into an electrical signal. The electrical signal is transmitted to the power amplifier 160 and displayed on the oscilloscope 170.

The strings 130 and 131, as described in ASTM C623-92 (2005), can be cotton thread, silica glass fiber thread, Nichrome, or platinum wire. However, ASTM C623-92 (2005) warns that spurious frequencies inherent in the described system may become apparent at temperatures above 600° C. These strings are preferably positioned at or close to the specimen's fundamental nodes.

The specimen 140 to be measured according to ASTM C623-92 (2005) should be solid isotropic material, rectangular or circular in cross section and between 120 by 25 by 3 mm for rectangular bars, or 120 by 4 mm for circular cross section specimens. The size of the specimens is important for successfully measuring the elastic modulus of glass or glass-ceramic materials because the measured resonance frequencies should fall within the range of frequencies within the measurement range of the equipment. ASTM C623-92 (2005) states that specimens of this size should produce a fundamental flexural resonance frequency in the range of from 1000 to 2000 Hz. Formulas 4 and 5 provide calculations of Young's modulus, or E, in general and for the specific geometry of a rectangular bar specimen respectively. These formulae can be adjusted to take into consideration different geometries of specimens in the measurement apparatus.

Elastic modulus or Young's Modulus can be calculated based on measurement taken using the apparatus described in FIG. 1 by the formula:

$$M = K w f_M^2 \qquad \text{Formula 4}$$

Where:

M=elastic modulus,

K=factor dependent on the dimensions of the bar and the particular characteristic vibration being investigated, w=weight of the bar; and, $f_M$=frequency(Hz) of the characteristic vibration.

Applying this general formula to ASTM C623-92 (2005) yields the following formula for a solid rectangular bar:

$$E = 96.517 (L^3/bt^3) T_1 w f^2 \times 10^{-8} \qquad \text{Formula 5}$$

Where:

96.517=a correction factor for the geometry of the rectangular bar, and the units used, E=Young's modulus (kfg/cm²), L=length of the bar, cm, b=width of the bar, cm, t=thickness of the bar, cm, w=weight of the bar, g, f=resonance frequency of the bar, Hz, and;

$T_1$=correction factor for fundamental flexural model to account for finite thickness of bar and Poisson's ratio.

Changing the units of measure from kgf/cm² (Kilo Pascals or KPa) to Pascals (Pa) and the units of measure from cm to mm yields the equivalent formula in ASTM C1198-01 as follows:

$$E = 0.9465 (m f_f^2 / b)(L^3/t^3) T_1 \qquad \text{Formula 6}$$

Where:

E=Young's modulus, Pa (N/m²),

L=length of the bar, mm, b=width of the bar, mm, t=thickness of the bar, mm, m=mass of the bar, g, $f_f$=fundamental resonance frequency of the bar, Hz, and;

$T_1$=correction factor for fundamental flexural model to account for finite thickness of bar, Poisson's ratio μ=Poisson's ratio.

$T_1$ can be calculated according Formula 7 as follows:

$$T_1 = 1 + 6.585(1 + 0.0752\mu + 0.8109\mu^2)(t/L)^2 - 0.868(t/L)^4 - \left[\frac{8.340(1 + 0.2023\mu + 2.173\mu^2)(t/L)^4}{1.000 + 6.338(1 + 0.1408\mu + 1.536\mu^2)(t/L)^2}\right]$$ Formula 7

Units can be changes from Pascals to pounds per square inch (psi) according to Formula 8 as follows:

Pa/6894.757=psi.  Formula 8

Figure 2:
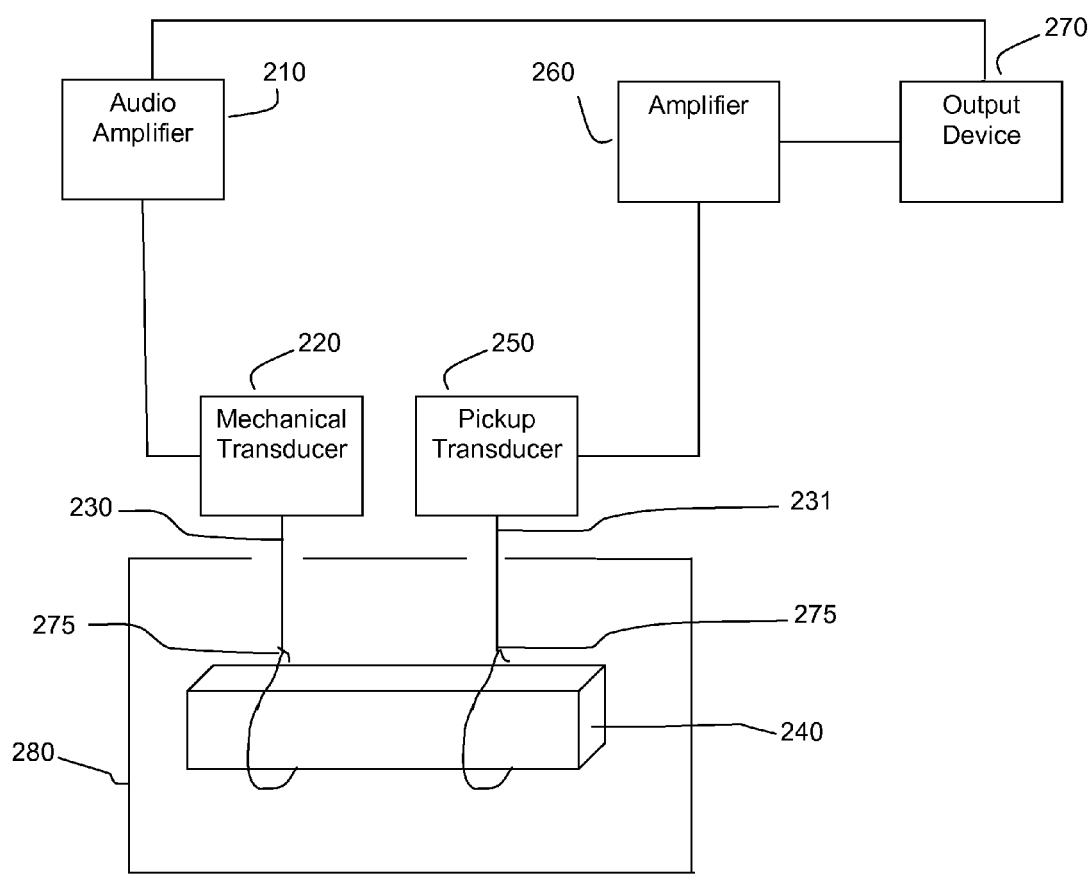
FIG. 2 is a block diagram of the test apparatus of the present invention for measuring the elastic modulus of a non-solid ceramic material.

FIG. 2 illustrates a block diagram of the test apparatus of the present invention for measuring the elastic modulus of a non-solid ceramic material. As illustrated in FIG. 2, an audio amplifier 210 is connected to a mechanical transducer 220. The mechanical transducer 220 converts an electrical signal from the audio amplifier to a mechanical vibration signal. A specimen 240 is suspended from the mechanical transducer 220 by a string or thread 230 on one end and from a pickup transducer 250 on another end by a second length of string or thread 231. The pickup transducer 250 is connected to an amplifier 260, which is connected to an output device 270 such as a computer or an oscilloscope. The strings or threads 230 and 231 may have two knots 275, one to form the loop which holds the specimen (shown in FIG. 2), and one which forms a loop which connects to the mechanical transducer 220 (not shown) or the pickup transducer (shown in FIGS. 3 and 4).

An electrical frequency signal, originating through the audio amplifier 210 is transmitted to the transducer 220 which converts the electrical signal from the audio amplifier 210 into a mechanical signal. The audio amplifier 210 may also be connected to the output device 270 to allow the output device or computer to control and display this initial frequency information in association with resonance information measured using the apparatus illustrated in FIG. 2. In the present invention, the mechanical transducer 210 is not a magnetic cutting head as is shown in FIG. 1. These devices were readily available when music was recorded onto vinyl, but are obsolete and difficult to source in the age of digital recording. In embodiments of the present invention, instead of a magnetic cutting head, a minishaker is used as the transducer 220. The minishaker, such as those available through Ling Dynamic Systems (LDS, Royston, Herts, England) model number V200 or Bruel & Kjaer (B&K Norcross, Ga.) type 4810, converts the frequency modulated electrical signal from the audio amplifier 210 into a mechanical vibration signal. These minishakers may have a threaded opening into which a screw hook is screwed so that a loop of silica yarn can be suspended from the vibrating diaphragm of the minishaker or vibrator or mechanical transducer.

The mechanical transducer 220 must be capable of translating electrical signals into mechanical signals. In addition, the mechanical transducer 220 must be able to support the weight of the specimen 240, suspended by strings 230 and 231 from the mechanical transducer 220 and the pickup transducer 250 (see FIGS. 3 and 4).

In an embodiment of the present invention, a length of silica yarn 230 is tied to the minishaker 220 at one end and looped around a specimen 240 at the other end. A length of approximately 2 feet of silica yarn is looped and tied at each end. To form the loop which will be used to suspend the specimen, the yarn is looped, tied in a square knot, and tightened to form an appropriately sized loop to hold the specimen. To form the loop which will be used to hang the string from the mechanical transducer and the pickup transducer, a slipknot is tied, and the loop is adjusted to an appropriate size. When the appropriate size is achieved, a square knot is tied. The yarn is then trimmed to remove any unnecessary material before the apparatus is assembled. The final length of silica yarn, with loops tied at each end, may be approximately 12 inches in length.

The vibration signal generated by the minishaker 220 is communicated through the silica yarn 230, to the specimen 240. In an embodiment of the present invention, the silica yarn is between 0.005 and 0.5 inches in diameter. In an embodiment of the present invention, the silica yarn is 0.02 inch diameter SY1-UC silica yarn available from EMTECH (Sterling Heights, Mich.). SY1-UC yarn is 0.02 inch in diameter, with 130 twists/meter, a tex number of 170, a breaking strength of 4 kg/ft and is 94-96% silica. At the other end of the specimen 240, another length of silica yarn 231 is looped around the specimen at one end and attached to a receiving transducer 230 at its other end.

Figure 5:
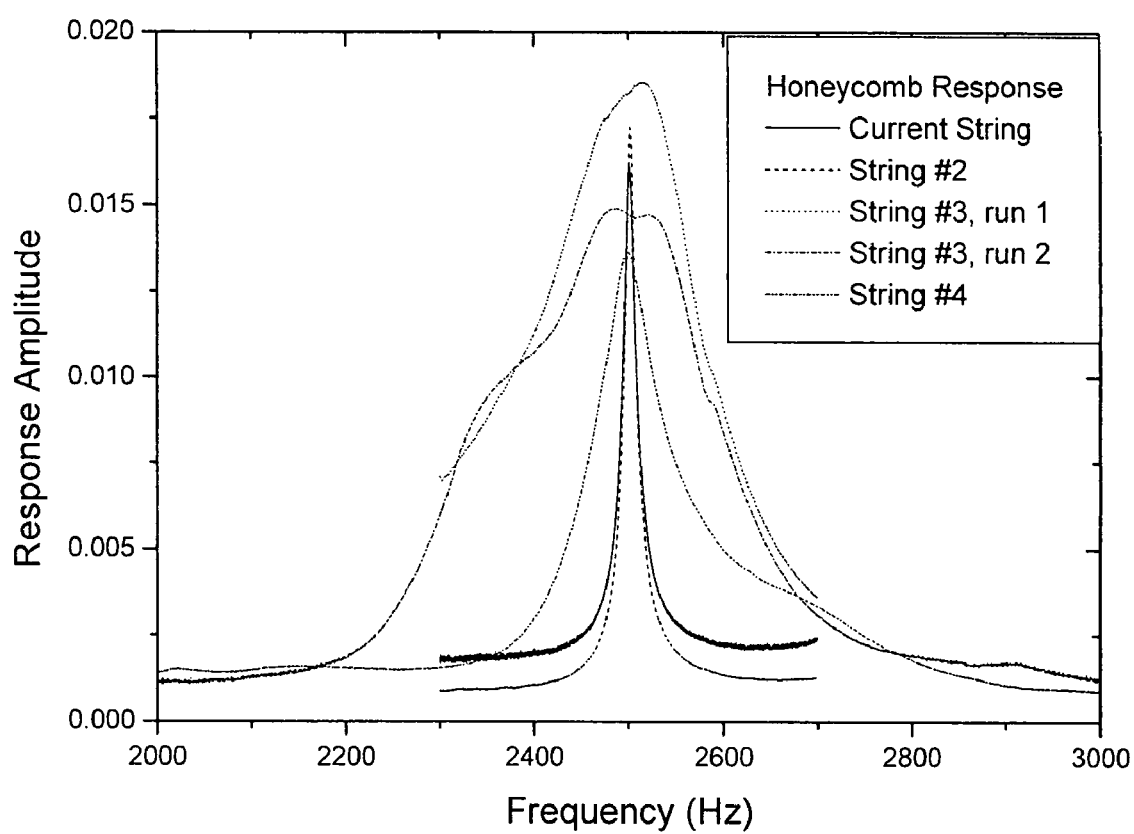
FIG. 5 is a graph illustrating the performance of different types of strings in embodiments of the present invention.

The specimen is suspended by two lengths of string or thread at two places along the length of the specimen. ASTM standard 1198 FIG. 5 illustrates the preferred locations of these suspension points at or near the flexural nodes of the specimen (0.224 fractional distance from each end of the suspended specimen).

The silica yarn is an important element of the apparatus for the measurement of elastic modulus of non-solid specimens, especially at high temperatures. The silica yarn must be able to deform sufficiently to conform to the dimensions of the specimen, so that it makes sufficient contact with the specimen to be able to transmit vibration signals from the minishaker to the specimen and from the specimen to the pickup transducer. In addition, the string or thread must also be able to hold a knot with sufficient strength to support the suspended specimen. And, the material must not allow the knot to slip once tied. This material must also be able to withstand significant temperature variations. For example, the temperature of the test apparatus may increase from room temperature (approximately 23° C.) to 1200° C. The material used to suspend the specimen 240 must be able to withstand such temperature changes without melting, without losing the strength required to suspend the specimen, without losing flexibility, and without changing its ability to transmit vibration signals from the minishaker to the specimen or from the specimen to the pickup. The strings or threads themselves may introduce significant broadening of the resonance peak measurements, and may cause the apparatus to fail to present measurable peak resonance for accurate calculations of elastic modulus.

In embodiments, the silica yarn may be a silica yarn that is 90-99% silica, with between 100 and 150 twists/meter, a breaking strength of between 3 and 6 kg/ft and a tex number of between 150 and 190.

The specimen 240 is illustrated as a rectangular block of non-solid ceramic honeycomb material. In embodiments, the ceramic honeycomb material may be different geometric shapes and may be made of cordierite silicon carbide, aluminum titanate, mullite or other materials. The material may be coated or uncoated, fired or green. The specimen itself is preferably structured and arranged to fit in the test apparatus, and to hang suspended by the silica yarn inside a furnace without contacting the internal surfaces of the furnace. The specimen is structured and arranged to work within the sensitivity range of the equipment. In embodiments, the specimen may be between 1.5 and 2.5 cm in width, between 0.5 and 1.6 cm in thickness, and between 8 and 20 cm in length. In other embodiments, the specimen may be approximately between 1.5 and 2 cm in width, between 1 and 1.5 cm in thickness and between 11 and 16 cm in length. The specimen may be a green or fired honeycomb structure. Acceptable dimensions of the specimen may be affected by additional considerations such as the wall thickness of honeycomb cell walls, the cell size, whether the honeycomb structure is coated or uncoated, and the honeycomb material.

Referring now to FIG. 2, the second length of silica yarn loops around the specimen 240 at one end and at the other end is attached to the pickup transducer 250. While the comparative example, illustrated in FIG. 1, shows that the pickup transducer is a crystal phonograph cartridge (see FIG. 1, 150), crystal phonograph cartridges are not preferable for the elastic modulus measurement apparatus of the present invention. Phonographs are no longer the preferred method of recording and storing music, and crystal phonograph cartridges are no longer readily available in the marketplace. In general, more modern phonograph cartridges are not strong enough to support the weight of the specimen, hanging from the phonograph cartridge by the second loop of silica yarn. These more modern phonograph cartridges are generally too sensitive to perform accurately in this apparatus. Older phonograph cartridges, for example those from the 1950's and 1960's provide acceptable utility in this apparatus, but are extremely difficult to find.

Figure 3:
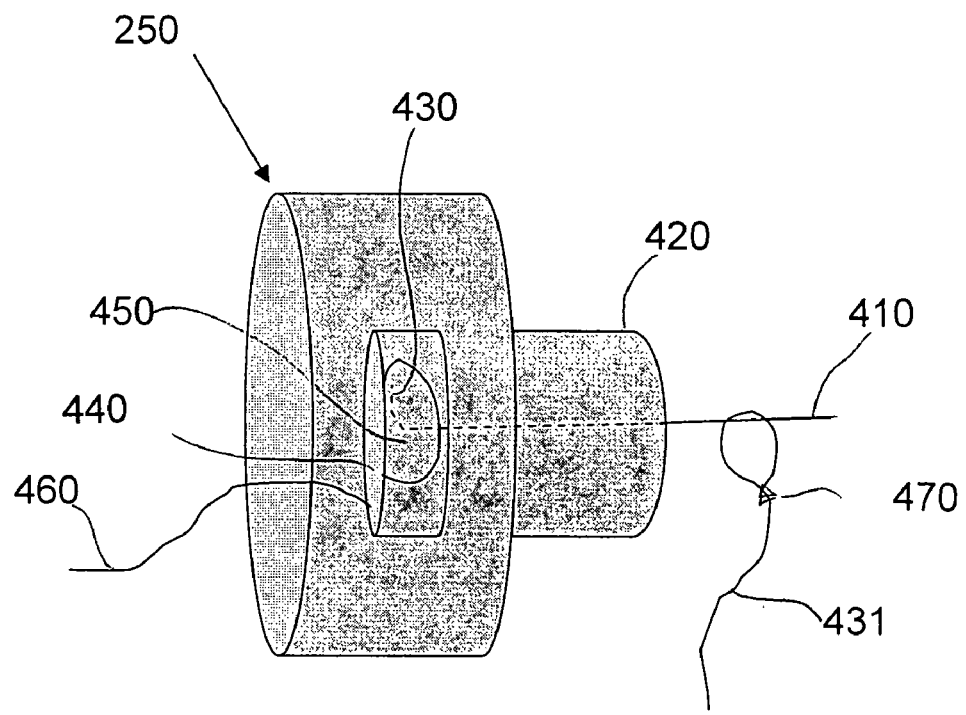
FIG. 3 is an illustration of an embodiment of the pickup transducer, a modified earphone.

In embodiments of the present invention, the pickup transducer 250 may be a modified earpiece or a modified hooked earpiece or part number MK4 available from Grindosonic (Mk 5.0, Lemmens, Belgium). FIG. 3 illustrates an embodiment of the pickup transducer 250, a modified earpiece or earphone. The modified earphone pickup transducer 250 has a metal wire 410 which extends into the ear-end 420 of the modified earphone 250. The metal wire 410 is bent at one end. The bent end 430 of the metal wire 410 is attached to the diaphragm 440 of the modified earphone 250. The metal wire 410 may be attached to the diaphragm 440 by a bead of epoxy 450 such as "double/bubble epoxy available from Hardman or Royal Adhesives & Sealants, LLC or Epoxy 907 from Miller-Stephenson or by any attachment means. A loop is formed in the silica yarn 431 by a know 470 and the silica yarn 431 is suspended from the metal wire 410 at one end. The modified earphone is connected to an amplifier by an electrical cord 460.

Vibration signals are transmitted from the specimen to the metal wire 410 via the silica yarn 431. Using this system, a vibration signal is transformed into an electrical signal by the pickup transducer 250. Like the minishaker, the modified earpiece pickup transducer 250 must be robust enough to support the weight of the specimen hanging from the silica yarn 431 looped around the wire 410 which is glued 450 to the diaphragm 440 of the modified earphone 250, and yet sensitive enough to measure the vibration signal generated from the specimen.

Figure 4:
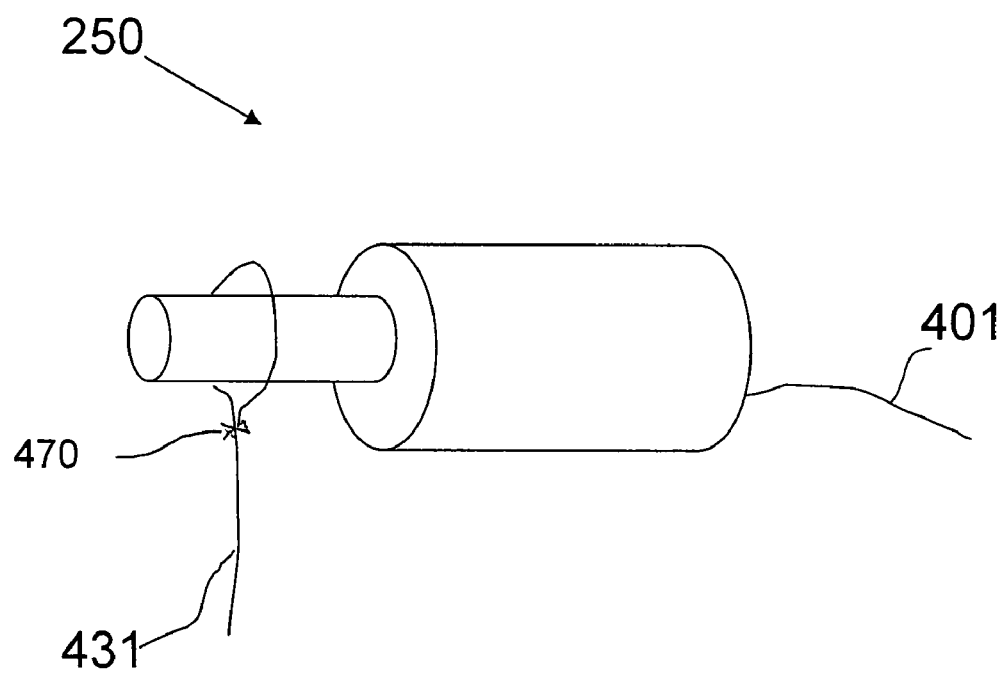
FIG. 4 is an illustration of an alternative embodiment of the pickup transducer.

In the alternative, the pickup transducer 250 may be a part number MK4 pickup available from Grindosonic (Mk 5.0, Lemmens, Belgium), shown in FIG. 4. As shown in FIG. 4, silica yarn 431 may be looped to the pickup transducer 250. The pickup transducer 250 may be connected to an amplifier or directly to an output device as shown in FIG. 2.

Turning again to FIG. 2, the frequency-regulated electrical signal that was generated by the audio amplifier 210, and translated into a mechanical vibration signal by the driver transducer or minishaker 220 is passed to the specimen 240 via a first length of silica yarn 230. This frequency signal creates a resonance vibration in the specimen 240 as a function of the geometry of the specimen, the applied frequency, the temperature, as well as its elastic modulus. The resonance vibration signal that has been generated in the specimen 240 is then communicated to the second length of silica yarn 231 through the contact between the specimen 240 and the silica yarn 231. The second length 231 of silica yarn then transmits the vibration signal to the pickup transducer 250 through the contact between the silica yarn 231 and the pickup transducer 250. In embodiments, the pickup transducer 250 can be either a modified earpiece as shown in FIG. 3, or a pickup transducer device as sold by Grindosonic (part number MK4), as shown in FIG. 4. The pickup transducer 250 translates the resonance vibration signal into an electrical signal which is amplified by an amplifier 260. The amplified electrical resonance signal is then communicated to an output device 270. In embodiments, the output device can be an oscilloscope, or a computer or processor.

In embodiments of the present invention, while the amplifiers 210 and 260, the minishaker 220, the pickup transducer 250 and the output device 270 are at room temperature, the specimen may be suspended in an oven or furnace 280. The oven 280 may be connected to the output device or computer 270 so that the computer can display the temperature ranges along with the resonance frequencies measured from the specimen.

The elastic modulus measurements made using the methods and apparatus of the present invention may be thought of not just as material measurements, but as structural measurements. For example, two samples, each made of the same material but having different structures, will have different values for elastic modulus. For example, a cordierite honeycomb specimen having 600 cells per square inch will have a different measured elastic modulus than a cordierite honeycomb specimen having 900 cells per square inch. Differences in the thickness of the cell walls within the honeycomb cordierite body will provide different measured elastic modulus values. Therefore, the elastic modulus values calculated using the methods and apparatus of the present invention can be thought of as structural elastic modulus measurements.

The apparatus and methods discussed above can be further understood in view of the following examples.

EXAMPLE 1

Thread Analysis

An experiment was performed to analyze the characteristics of different threads or strings for use in the apparatus and methods of the present invention. A honeycomb specimen was suspended in the apparatus of the present invention, where the minishaker was an LDS V200 minishaker and the pickup transducer was a Grindosonic MK4 part. A frequency sweep was applied to each thread and a resonance frequency was detected. Four threads were analyzed. FIG. 5 is a graph illustrating the performance of four different types of threads or strings in embodiments of the present invention. Additional threads could not be measured, due to their inability to form a suitable supporting knot for the suspension of the specimen.

The current string or thread, a 0.02 inch diameter SY1-UC silica yarn available from EMTECH (Sterling Heights, Mich.) conducted the input frequency and the resonance frequency efficiently, resulting in a sharp measured peak. Thread or string #2 is Saint-Gobain Quartzel® thread 300-2/4 QS13 4Z 3.8S. This material also resulted in a sharp peak. String 3 is silica yarn 33×16 (Ametek, Paoli, Pa.). String #4 is C100-3 (Refrasil® manufactured by Hitco Carbon Composites, Inc. Gardena, Calif.). Strings #3 (run two times) and #4 were unacceptable materials for the methods of the present invention. String #3 was run two times. In the two experiments, String #3 resulted in different peak frequencies. In addition, in both experiments, String #3 resulted in a double peak. String #4 resulted in a peak frequency which appears accurate. However, String #4 did not provide as sharp a peak frequency measurement. The use of String #3 and String #4 would result in unacceptably indefinite peak frequency measurements, and introduce unacceptable levels of error into calculated elastic modulus measurements.

EXAMPLE 2

Resonance Measurements of a Cordierite Honeycomb Specimen

Figure 6:
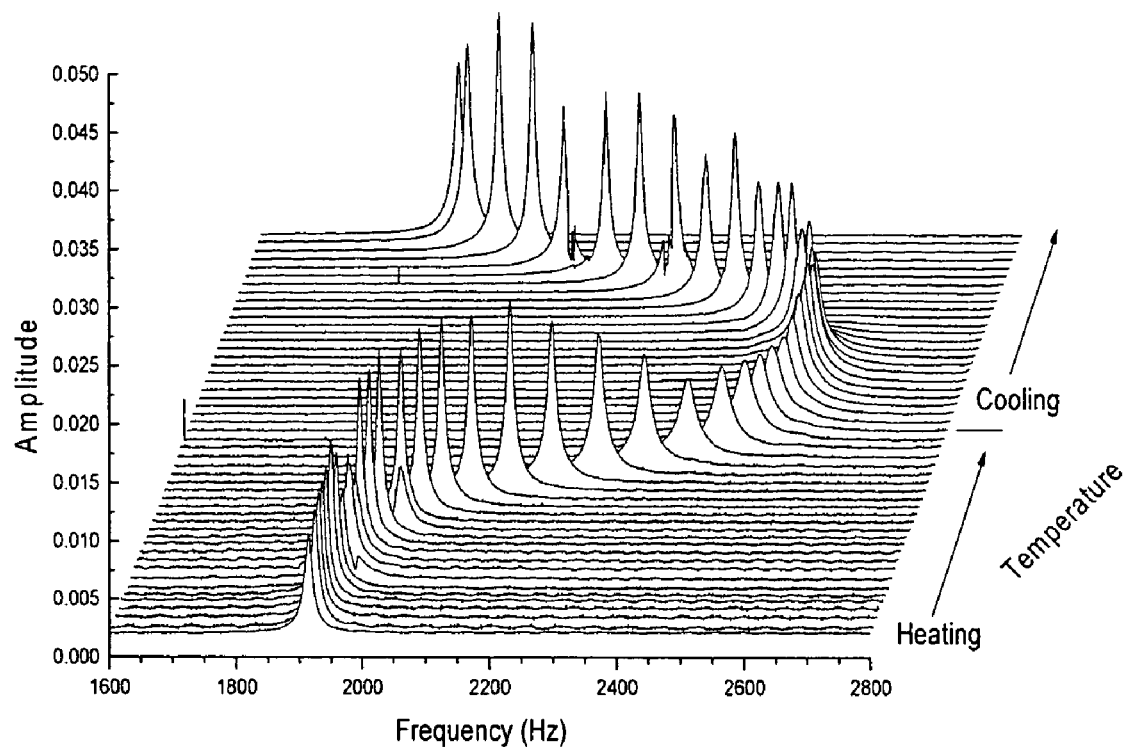
FIG. 6 is a waterfall plot of resonance data from a cordierite sample as measured by elastic modulus measurement apparatus and method of the present invention.

FIG. 6 is a waterfall plot of resonance data measured by the variable-temperature elastic modulus measurement method and apparatus of the present invention. The measurements illustrated in FIG. 6 were taken using the apparatus illustrated in FIG. 2, where the mechanical transducer is a minishaker (LDS V200), the pickup transducer is a Grindosonic MK4 part, and the thread is EMTECH SY1-UC silica yarn 0.02 inch diameter (Sterling Heights, Mich.). The plot illustrates an embodiment of the output of the method of the present invention. The waterfall plot shows resonance frequencies of a honeycomb-shaped non-solid ceramic specimen over a range of frequencies from 2300 Hz to 4300 Hz, where each line represents this measurement taken at a different temperature, starting with room temperature (approximately 25° C.), increasing in 50° C. intervals until a peak temperature of 1200° C. is achieved. Measurements are then taken in 50° C. intervals as the temperature cools in the furnace. The waterfall plot offsets the sweep from each temperature slightly so that a "3D" appearance develops which helps the eye follow the data. Because of the imperfect cell geometry of a honeycomb ceramic material, (variations in wall thicknesses, lengths, broken walls, etc.) multiple resonances and multiple peaks may occur. Presenting data in a waterfall plot allows these imperfections to be shown.

Figure 7:
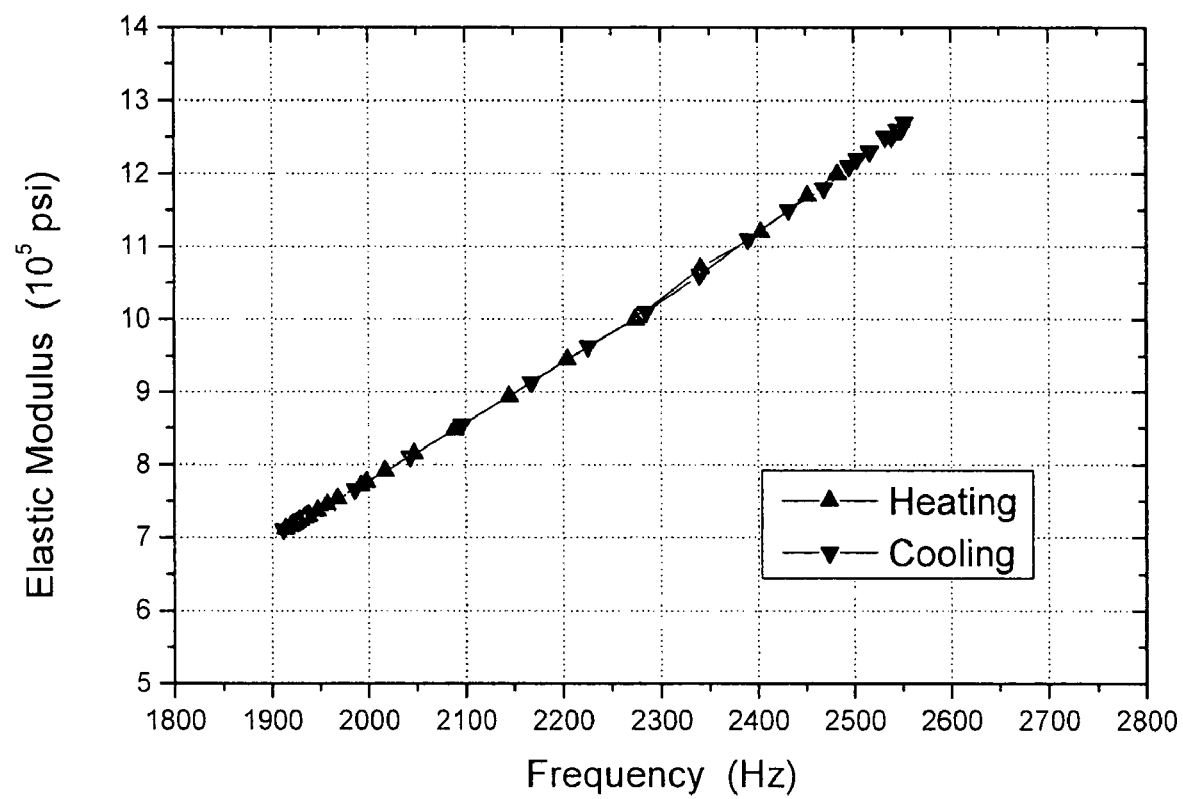
FIG. 7 is a graph showing the relationship between E, elastic modulus, and frequency as measured in a cordierite sample by the apparatus and method of the present invention.
Figure 8:
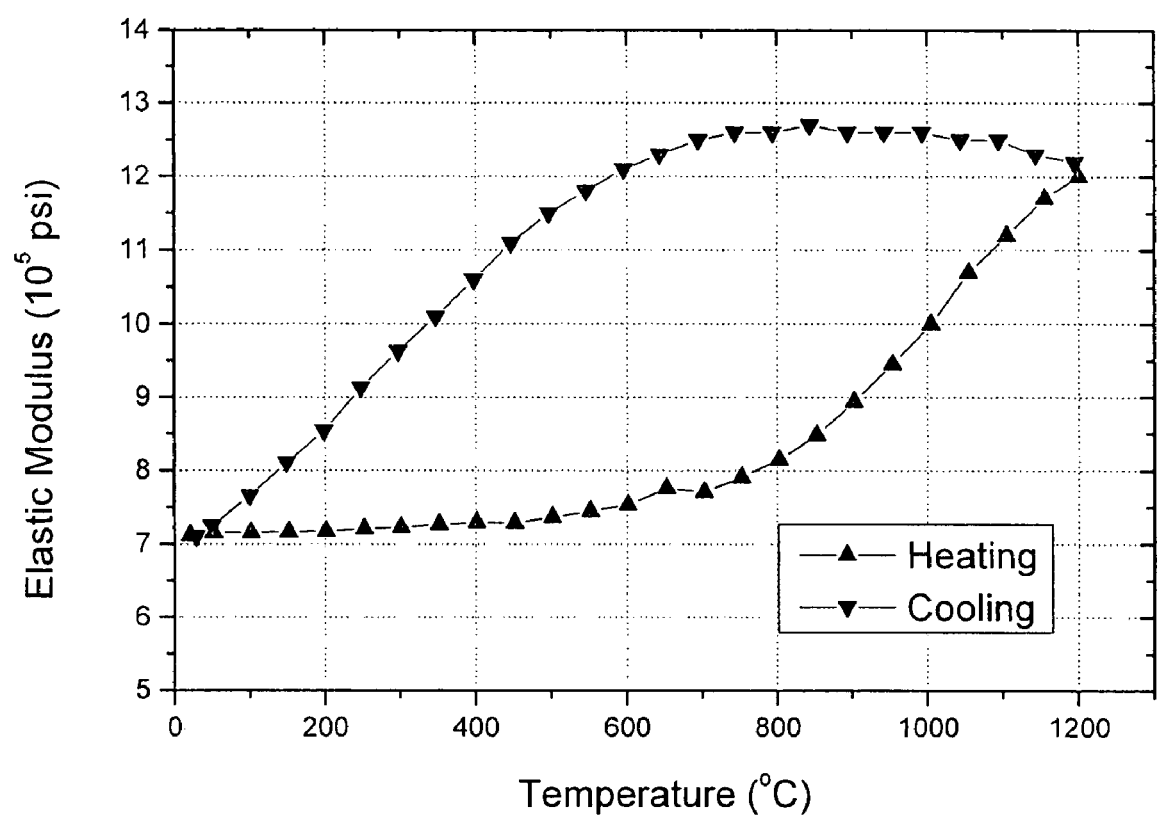
FIG. 8 is a graph showing the relationship between E, elastic modulus and temperature as measured in a cordierite sample by the apparatus and method of the present invention.

For the waterfall plot shown in FIG. 6, the sweep time, or period, i.e. the time to sweep from a below resonant frequency to a frequency above the resonance, was adjusted to allow for quasi-equilibrium vibration for accuracy. Table 1 reports the temperature, measured peak frequency and calculated Young's Modulus as shown in FIGS. 6, 7 and 8.

Young's modulus was calculated according to Formula 6, and converted to psi from Pascals according to Formula 8. $T_1$ was calculated according to Formula 7, with an estimated Poisson's ratio of 0.25. For example, data shown in FIGS. 6, 7 and 8 was obtained from a specimen which had a length (L) of 129.75 mm, a width (b) of 27.17 mm, a thickness (t) of 9.44 mm, a mass (m) of 14.285 g, and an estimated Poisson's ratio of 0.25. Given these parameters, Formula 6 can be solved as follows: $E=[0.9465\ (mf_f^2/b)(L^3/t^3)T_1]/6894.757$.

The calculated elastic modulus (E) is presented in Table 1:

TABLE 1

| Temperature (C.°) | Peak Freq(Hz) | Young's Modulus(psi) | Temperature (C.°) | Peak Freq(Hz) | Young's Modulus(psi) |
|---|---|---|---|---|---|
| 21 | 1914 | 7.12E+05 | 1194 | 2503 | 1.22E+06 |
| 52 | 1920 | 7.16E+05 | 1143 | 2516 | 1.23E+06 |
| 102 | 1920 | 7.16E+05 | 1094 | 2532 | 1.25E+06 |
| 152 | 1921 | 7.17E+05 | 1044 | 2539 | 1.25E+06 |
| 202 | 1922 | 7.18E+05 | 993 | 2545 | 1.26E+06 |
| 253 | 1926 | 7.21E+05 | 943 | 2548 | 1.26E+06 |
| 302 | 1929 | 7.23E+05 | 894 | 2549 | 1.26E+06 |
| 353 | 1934 | 7.27E+05 | 844 | 2552 | 1.27E+06 |
| 402 | 1938 | 7.30E+05 | 794 | 2546 | 1.26E+06 |
| 452 | 1937 | 7.29E+05 | 744 | 2546 | 1.26E+06 |
| 502 | 1947 | 7.37E+05 | 695 | 2532 | 1.25E+06 |
| 552 | 1957 | 7.45E+05 | 644 | 2516 | 1.23E+06 |
| 602 | 1968 | 7.53E+05 | 596 | 2495 | 1.21E+06 |
| 653 | 1998 | 7.76E+05 | 546 | 2469 | 1.18E+06 |
| 703 | 1992 | 7.71E+05 | 497 | 2432 | 1.15E+06 |
| 753 | 2017 | 7.91E+05 | 447 | 2390 | 1.11E+06 |
| 803 | 2047 | 8.15E+05 | 398 | 2340 | 1.06E+06 |
| 853 | 2089 | 8.48E+05 | 348 | 2285 | 1.01E+06 |
| 903 | 2145 | 8.94E+05 | 298 | 2226 | 9.63E+05 |
| 954 | 2205 | 9.45E+05 | 248 | 2168 | 9.13E+05 |
| 1005 | 2274 | 1.00E+06 | 199 | 2096 | 8.54E+05 |
| 1055 | 2341 | 1.07E+06 | 149 | 2043 | 8.11E+05 |
| 1105 | 2403 | 1.12E+06 | 100 | 1986 | 7.66E+05 |
| 1155 | 2452 | 1.17E+06 | 50 | 1932 | 7.25E+05 |
| 1200 | 2483 | 1.20E+06 | 29 | 1912 | 7.11E+05 |

FIG. 7 is a graph showing the relationship between E, elastic modulus, and frequency as measured in a cordierite sample by the apparatus and method of the present invention. FIG. 7 illustrates that, using the apparatus and method of the present invention, it is possible to measure peak frequencies in a non-solid cordierite specimen having a honeycomb structure, and to use those measured peak frequencies to calculate E values.

FIG. 8 is a graph showing the relationship between E, elastic modulus and temperature as measured in a cordierite sample by the apparatus and method of the present invention. FIG. 8 illustrates that the calculated elastic modulus for this cordierite specimen increased gradually, and then more steeply, with increasing temperature up to 1,200° C. As the specimen cooled from 1,200° C. to around 800° C. the elastic modulus remained high, with a gradual and then more rapid decrease between around 800° C. and room temperature. These changes are believed to be due in part to microcracking in the specimen. The increase in elastic modulus is believed to be due a re-closing, and eventual annealing, of microcracks in the cordierite ceramic material during heating, so that the material has progressively fewer open microcracks, therefore is more rigid, exhibiting a higher elastic modulus, at higher temperatures. These microcracks may re-open as the material cools below about 800° C. The ability to measure elastic modulus in these non-solid specimens, through an extended temperature range, using the methods and apparatus of the present invention, allows for an understanding of the microstructure of a material that might not otherwise be measurable.

EXAMPLE 3

Resonance Measurements of an Aluminum Titanate Honeycomb Specimen

Figure 9:
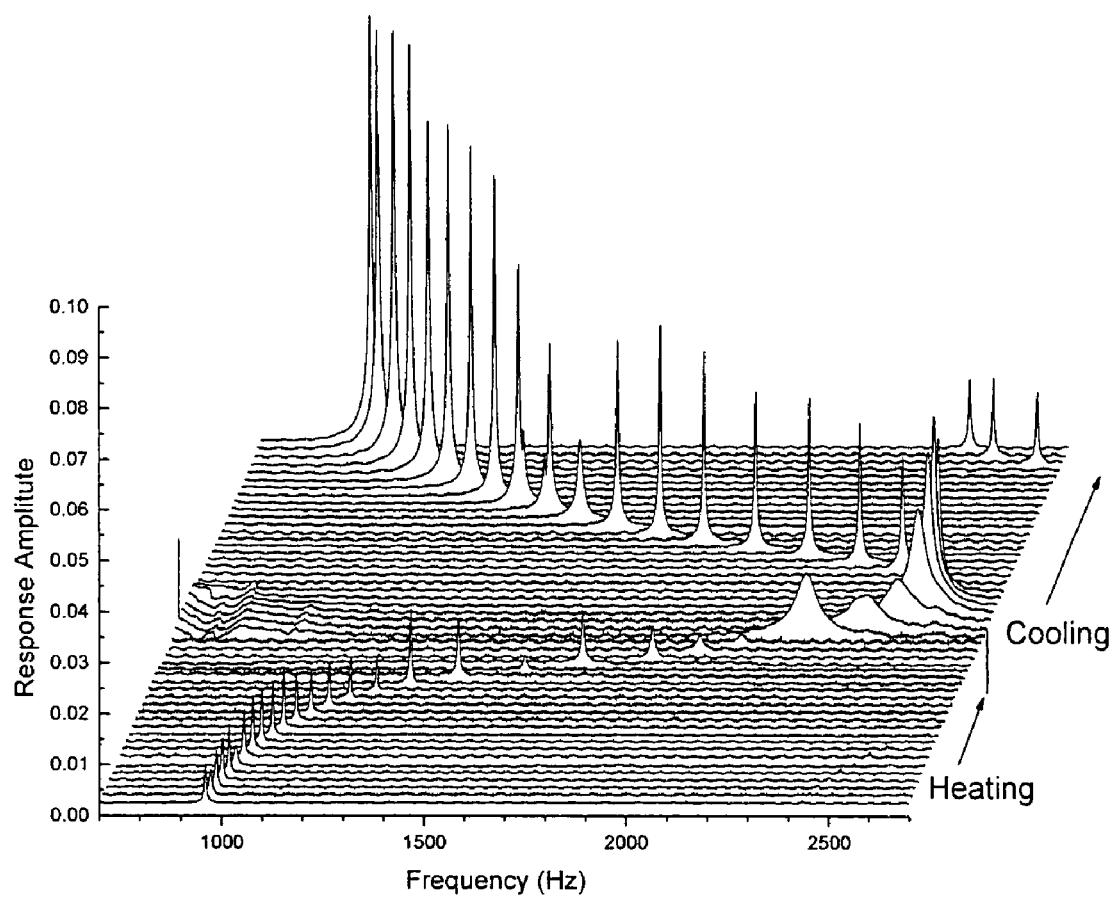
FIG. 9 is a waterfall plot of resonance data from an aluminum titanate sample as measured by the elastic modulus measurement apparatus and method of the present invention.
Figure 10:
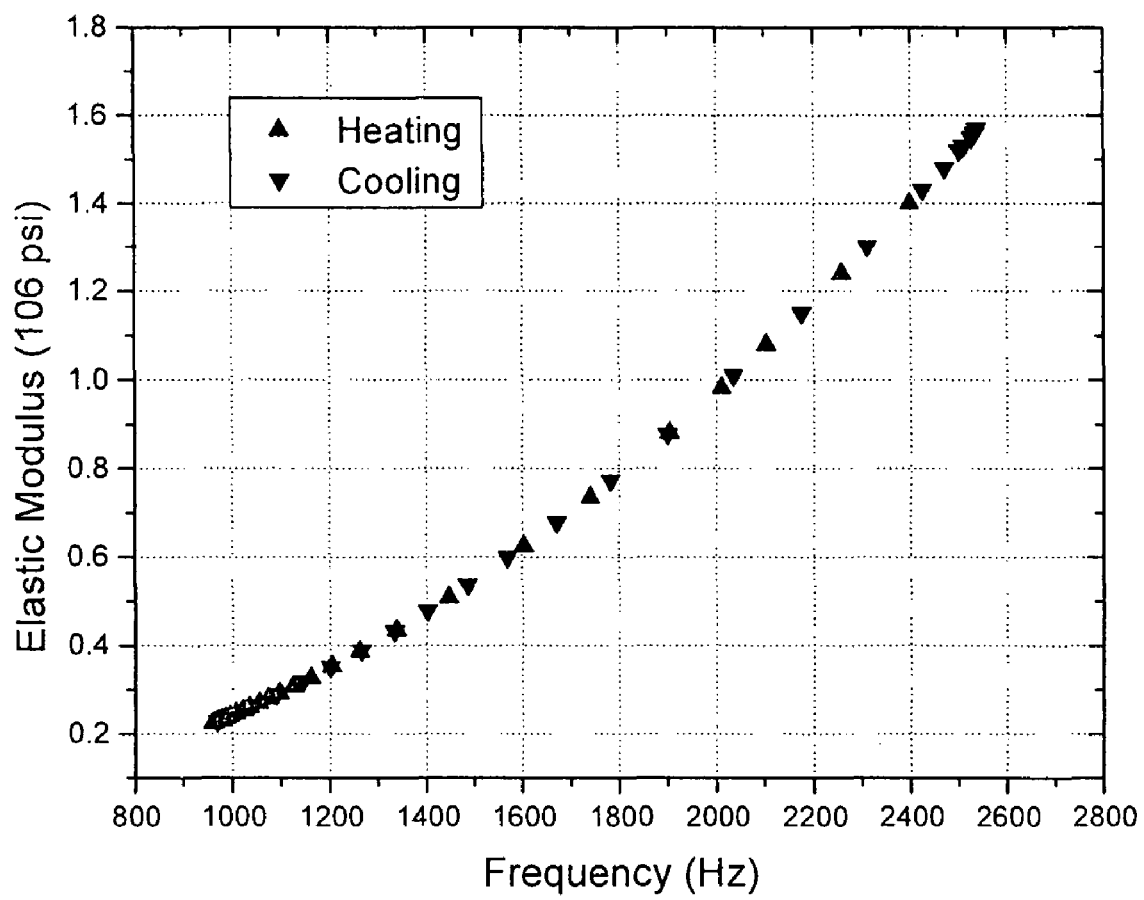
FIG. 10 is a graph showing the relationship between E, elastic modulus, and frequency as measured in an aluminum titanate sample by the apparatus and method of the present invention.
Figure 11:
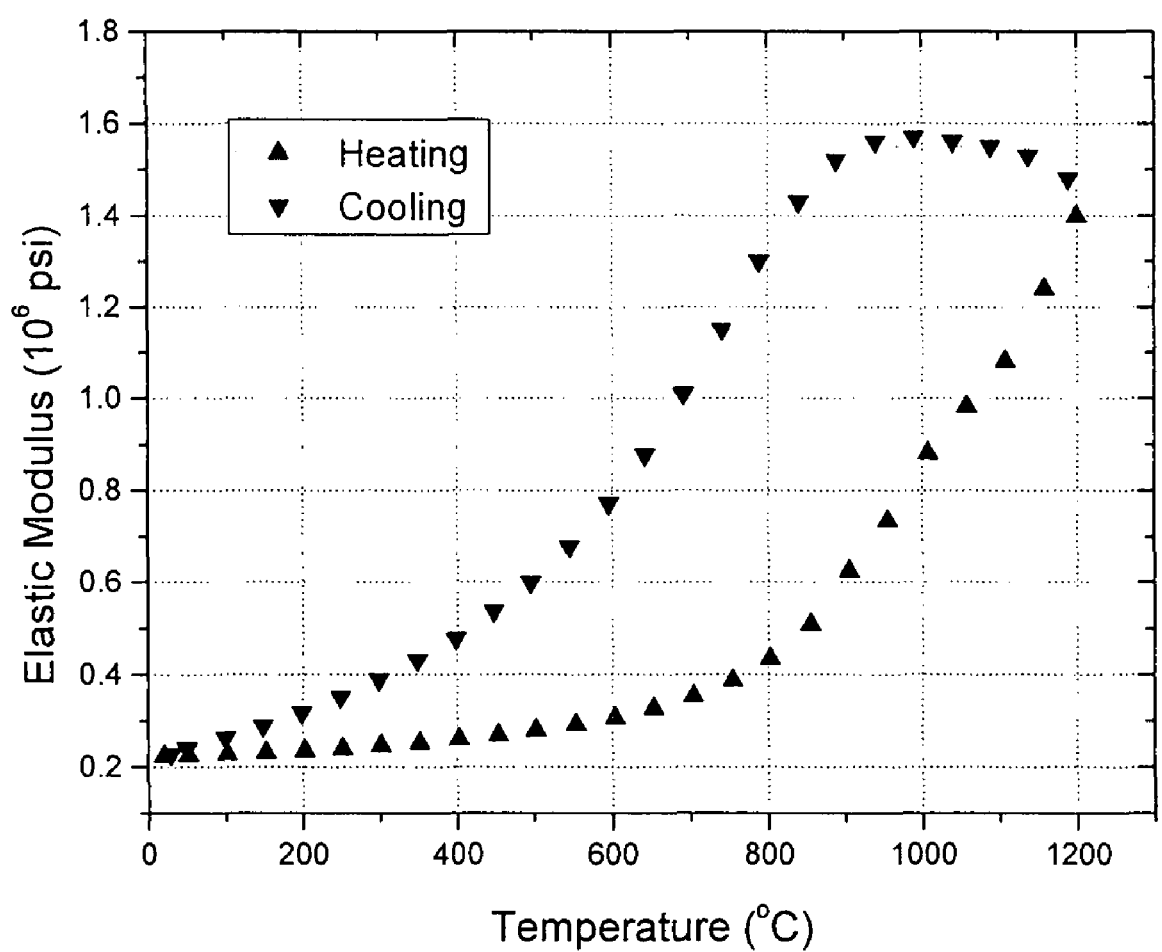
FIG. 11 is a graph showing the relationship between E, elastic modulus and temperature as measured in an aluminum titanate sample by the apparatus and method of the present invention.

FIG. 9 is a waterfall plot of resonance data from an aluminum titanate sample as measured by elastic modulus measurement apparatus and method of the present invention. The measurements illustrated in FIG. 9 were taken using the apparatus illustrated in FIG. 2, where the mechanical transducer is a minishaker (LDSV200), the pickup transducer is a Grindosonic MK4 part, and the thread is EMTECH SY1-UC silica yarn 0.02 inch diameter (Sterling Heights, Mich.). The plot illustrates an embodiment of the output of the method of the present invention. The waterfall plot shows resonance frequencies of a honeycomb-shaped non-solid aluminum titanate ceramic specimen over a range of frequencies from 700 Hz to 2700 Hz, where each line represents this measurement taken at a different temperature, starting with room temperature (approximately 25° C.), increasing in 50° C. intervals until a peak temperature of 1200° C. was achieved. Measurements were then taken in 50° C. intervals as the temperature cooled in the furnace. The waterfall plot offset the sweep from each temperature slightly so that a "3D" appearance developed which helps the eye follow the data. Table 2 reports the temperature, measured peak frequency and calculated Young's Modulus as shown in FIGS. 9, 10 and 11.

Young's modulus was calculated according to Formula 6, $T_1$ was calculated according to Formula 7 (with an estimated Poisson's ratio of 0.25) and converted to psi from Pascals according to Formula 8. For example, the specimen shown in FIGS. 9, 10 and 11 had a length (L) of 152.48 mm, a width (b) of 23.31 mm, a thickness (t) of 15.2 mm, a mass (m) of 38.2257 g, and an estimated Poisson's ratio of 0.25. Given these parameters, Formula 6 can be solved as follows: $E=[0.9465(mf_f^2/b)(L^3/t^3)T_1]/6894.757$.

The calculated elastic modulus (E) of the aluminum titanate sample is presented in Table 2:

TABLE 2

| Temperature (C.°) | Peak Freq(Hz) | Young's Modulus(psi) | Temperature (C.°) | Peak Freq(Hz) | Young's Modulus(psi) |
|---|---|---|---|---|---|
| 21 | 960 | 2.24E+05 | 1189 | 2470 | 1.48E+06 |
| 52 | 965 | 2.26E+05 | 1138 | 2511 | 1.53E+06 |
| 102 | 971 | 2.29E+05 | 1089 | 2528 | 1.55E+06 |
| 153 | 978 | 2.32E+05 | 1040 | 2535 | 1.56E+06 |
| 203 | 986 | 2.36E+05 | 990 | 2538 | 1.57E+06 |
| 252 | 995 | 2.40E+05 | 940 | 2534 | 1.56E+06 |
| 302 | 1007 | 2.47E+05 | 889 | 2501 | 1.52E+06 |
| 352 | 1021 | 2.53E+05 | 840 | 2425 | 1.43E+06 |
| 403 | 1036 | 2.61E+05 | 790 | 2310 | 1.30E+06 |
| 454 | 1055 | 2.70E+05 | 741 | 2176 | 1.15E+06 |
| 503 | 1074 | 2.80E+05 | 692 | 2036 | 1.01E+06 |
| 554 | 1097 | 2.92E+05 | 643 | 1900 | 8.77E+05 |
| 604 | 1125 | 3.07E+05 | 596 | 1783 | 7.72E+05 |
| 654 | 1161 | 3.27E+05 | 546 | 1671 | 6.78E+05 |
| 704 | 1205 | 3.53E+05 | 496 | 1570 | 5.99E+05 |
| 754 | 1262 | 3.87E+05 | 448 | 1487 | 5.37E+05 |
| 803 | 1338 | 4.35E+05 | 399 | 1402 | 4.78E+05 |
| 855 | 1447 | 5.09E+05 | 349 | 1334 | 4.32E+05 |
| 905 | 1604 | 6.25E+05 | 299 | 1266 | 3.89E+05 |
| 956 | 1740 | 7.35E+05 | 249 | 1202 | 3.51E+05 |
| 1008 | 1904 | 8.81E+05 | 199 | 1144 | 3.18E+05 |
| 1058 | 2011 | 9.83E+05 | 149 | 1091 | 2.89E+05 |
| 1108 | 2105 | 1.08E+06 | 100 | 1042 | 2.64E+05 |
| 1159 | 2258 | 1.24E+06 | 50 | 995 | 2.41E+05 |
| 1200 | 2398 | 1.40E+06 | 30 | 969 | 2.28E+05 |

FIG. 10 is a graph showing the relationship between E, elastic modulus, and frequency as measured in an aluminum titanate sample by the apparatus and method of the present invention. FIG. 10 illustrates that, using the apparatus and methods of the present invention, it is possible to measure elastic modulus of a non-solid aluminum titanate specimen through a temperature range from room temperature to 1200° C.

FIG. 11 shows the relationship between E, elastic modulus and temperature as measured in an aluminum titanate sample by the apparatus and method of the present invention.

The ability to measure and visualize the physical characteristics of complex non-solid materials as in examples 2 and 3, and FIGS. 6-11, allows for more precise understanding of and characterization of the materials themselves. For example, a more porous ceramic material or a microcracked material will exhibit different measurements of elastic modulus or Young's modulus when measured in the apparatus of the present invention and according to the methods of the present invention compared to a non-microcracked material. Whether the materials are microcracked or cracked will be apparent with these kinds of measurements.

The foregoing description of the specific embodiments reveals the general nature of the invention that others can, by applying knowledge within the skill of the art, readily modify and/or adapt for various applications such specific embodiments, without undue experimentation and without departing from the general concept of the present invention. Such adaptations and modifications, therefore, are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method of measuring the elastic modulus of a non-solid ceramic material comprising:
    suspending a non-solid ceramic material from two silica threads;
    delivering a vibration signal to the non-solid ceramic material through one silica thread as the non-solid ceramic material is heated across a range of frequencies and across a range of temperatures between 20° C. and 1200° C.; and,
    measuring a vibration signal from the non-solid ceramic material through another silica thread across the range of frequencies and the range of temperatures.

2. The method of claim 1 further comprising measuring a vibration signal from the non-solid ceramic material while cooling the non-solid ceramic material through a range of temperatures between 1200° C. and 20° C.

3. The method of claim 1 further comprising recording the measured vibration signal.

4. The method of claim 1 further comprising plotting the amplitude of the measured vibration signal versus frequency.

5. The method of claim 1 wherein the vibration signal to the non-solid ceramic material is delivered by a minishaker.

6. The method of claim 1 wherein the vibration signal from the non-solid ceramic material is measured by a modified earphone.

7. The method of claim 1 wherein the silica yarn is between 0.005 and 0.5inches in diameter.

8. The method of claim 7 wherein the silica yarn is 0.02 inch diameter silica yarn.

9. The method of claim 1 wherein the ceramic material is cordierite or aluminum titanate.

10. The method of claim 1 further comprising plotting the amplitude of the measured vibration signal versus frequency.

11. the method of claim 10 further comprising identifying peak measured vibration signals.

12. The method of claim 11 further comprising calculating elastic modulus of the non-solid ceramic material as a function of the peak vibration signals measured through the heating of the non-solid ceramic material.

13. The method of claim 12 further comprising plotting the calculated elastic modulus as a function of temperature.

14. The method of claim 13 further comprising using a plot of calculated elastic modulus as a function of temperature of a non-solid ceramic material to characterize physical characteristics of a non-solid ceramic material.

15. The method of claim 14 wherein the physical characteristics comprise cracking, microcracking or a combination.

16. A method of characterizing elastic modulus in a non-solid ceramic material comprising:
   suspending a non-solid ceramic material from two silica threads;
   heating the non-solid ceramic material across a range of temperatures between 20° C. and 1200° C.;
   cooling the non-solid ceramic material across a range of temperatures between 1200° C. and 20° C.;
   delivering a plurality of vibration signals comprising a range of frequencies to the non-solid ceramic material through one silica thread while heating and cooling the non-solid ceramic material;
   measuring a plurality of vibration signals from the non-solid ceramic material through a second silica thread across the range temperatures;
   identifying a plurality of peak vibration signals;
   calculating elastic modulus of the non-solid ceramic material as a function of the peak vibration signals measured through the heating and cooling of the non-solid ceramic material; and,
   displaying the calculated elastic modulus as a function of temperature through the heating and cooling of the non-solid ceramic material.

17. The method of claim 16 wherein the display is an electronic display.

18. The method of claim 16 wherein the display is a plot of calculated elastic modulus versus temperature.

* * * * *